US012417822B2

(12) United States Patent
Morse et al.

(10) Patent No.: US 12,417,822 B2
(45) Date of Patent: Sep. 16, 2025

(54) MANAGEMENT AND COORDINATION OF DATA FOR DIGITAL THERAPEUTICS TRIALS

(71) Applicant: Click Therapeutics, Inc., New York, NY (US)

(72) Inventors: William Morse, New York, NY (US); Bailey Willis, New York, NY (US)

(73) Assignee: Click Therapeutics, Inc., New York, NY (US)

( * ) Notice: Subject to any disclaimer, the term of this patent is extended or adjusted under 35 U.S.C. 154(b) by 79 days.

(21) Appl. No.: 18/143,260

(22) Filed: May 4, 2023

(65) Prior Publication Data
US 2024/0371477 A1 Nov. 7, 2024

(51) Int. Cl.
G16H 10/20 (2018.01)
(52) U.S. Cl.
CPC .................... G16H 10/20 (2018.01)
(58) Field of Classification Search
CPC ........................................................ G16H 10/20
See application file for complete search history.

(56) References Cited

U.S. PATENT DOCUMENTS

| 10,484,845 | B2 * | 11/2019 | Khaleghi | H04W 4/14 |
| 10,653,361 | B2 * | 5/2020 | DeBates | A61B 5/082 |
| 10,725,652 | B2 * | 7/2020 | Bhavaraju | A61B 5/14503 |
| 10,861,595 | B2 * | 12/2020 | Satake | G16H 10/60 |
| 10,997,243 | B1 * | 5/2021 | Paulus | G06F 16/955 |
| 11,020,064 | B2 * | 6/2021 | Fountaine | G10L 25/66 |
| 11,036,735 | B2 * | 6/2021 | Butani | G06F 16/283 |
| 11,061,798 | B1 | 7/2021 | Jain et al. | |
| 11,082,487 | B1 * | 8/2021 | Jain | H04L 67/535 |
| 11,102,304 | B1 | 8/2021 | Jain et al. | |
| 11,222,071 | B1 * | 1/2022 | Paulus | G06F 16/908 |
| 11,228,875 | B2 * | 1/2022 | Khaleghi | G10L 25/63 |
| 11,233,759 | B2 * | 1/2022 | Gao | G06Q 30/0246 |
| D954,730 | S * | 6/2022 | Kaminski | D14/486 |
| 11,363,999 | B2 * | 6/2022 | Fountaine | G06F 3/167 |
| 11,404,062 | B1 * | 8/2022 | De | G06F 3/165 |
| 11,410,655 | B1 * | 8/2022 | De | G10L 15/30 |
| 11,462,307 | B2 * | 10/2022 | Satake | G06Q 50/22 |
| 11,494,438 | B2 * | 11/2022 | Paulus | G06F 16/9017 |

(Continued)

OTHER PUBLICATIONS

International Search Report and Written Opinion for PCT Appl. No. PCT/US2023/20982, mailed Jul. 21, 2023.

*Primary Examiner* — Michael I Ezewoko
(74) *Attorney, Agent, or Firm* — Foley & Lardner LLP

(57) ABSTRACT

Provided herein are systems and methods of managing access to data associated with trials for digital therapeutics on participants. A server can maintain a data storage for a plurality of phases associated with a trial for a digital therapeutic on participants. The data storage may include (i) a first portion of a plurality of datasets from the plurality of participants from one or more of the plurality of phases of the trial, and (ii) a second portion of the plurality of datasets from the digital therapeutics in at least one of the plurality of phases of the trial. The server can receive from a user device, a request identifying a phase of the plurality of phases for which the plurality of datasets is to be accessed. The server can select a corresponding portion of the plurality of datasets based on the request to provide the user device.

18 Claims, 8 Drawing Sheets

(56) References Cited

U.S. PATENT DOCUMENTS

| | | | | |
|---|---|---|---|---|
| 11,500,655 B2* | 11/2022 | Ziraknejad | | G06F 16/248 |
| 11,521,736 B1* | 12/2022 | Gastfriend | | G16H 10/20 |
| 11,574,743 B1* | 2/2023 | Soza | | G16H 20/00 |
| 11,595,498 B2* | 2/2023 | Jain | | H04L 67/52 |
| 11,605,038 B1* | 3/2023 | Jain | | G06Q 10/06313 |
| 11,607,182 B2* | 3/2023 | Fountaine | | G16H 40/67 |
| 11,625,294 B2* | 4/2023 | Bramble | | G06F 11/0709 |
| | | | | 714/2 |
| 11,651,862 B2* | 5/2023 | Lure | | A61B 5/4088 |
| | | | | 705/2 |
| 11,664,099 B1* | 5/2023 | Jain | | G16H 40/67 |
| | | | | 705/2 |
| 11,682,390 B2* | 6/2023 | Temkin | | G10L 15/22 |
| | | | | 704/275 |
| 11,711,422 B1* | 7/2023 | Jain | | H04L 41/16 |
| | | | | 709/203 |
| 11,736,564 B1* | 8/2023 | Jain | | H04W 4/38 |
| | | | | 709/203 |
| 11,741,238 B2* | 8/2023 | Rioux | | G06F 21/54 |
| | | | | 726/23 |
| 11,749,390 B2* | 9/2023 | Satake | | G06Q 50/22 |
| 11,756,663 B2* | 9/2023 | Neumann | | G06N 20/20 |
| | | | | 705/3 |
| 11,765,249 B2* | 9/2023 | Erlingsson | | G06F 16/9024 |
| | | | | 709/224 |
| 11,770,398 B1* | 9/2023 | Erlingsson | | G06F 16/3329 |
| | | | | 709/224 |
| 11,785,104 B2* | 10/2023 | Erlingsson | | H04L 41/145 |
| | | | | 709/224 |
| 11,790,107 B1* | 10/2023 | Jain | | H04L 63/102 |
| | | | | 726/4 |
| 11,792,284 B1* | 10/2023 | Nanduri | | G06F 9/542 |
| | | | | 709/224 |
| 11,797,608 B2* | 10/2023 | Paulus | | G06F 16/24568 |
| 11,815,994 B2* | 11/2023 | Bramble | | G06F 11/0706 |
| 11,818,156 B1* | 11/2023 | Parikh | | G06F 16/9537 |
| 11,838,365 B1* | 12/2023 | Jain | | G16H 20/10 |
| 11,849,000 B2* | 12/2023 | Williams | | H04L 67/535 |
| 11,876,875 B2* | 1/2024 | Banerjee | | H04L 41/06 |
| 11,887,736 B1* | 1/2024 | Norgeot | | G16H 15/00 |
| 11,894,984 B2* | 2/2024 | Erlingsson | | H04L 63/1408 |
| 11,895,135 B2* | 2/2024 | Kapoor | | G06F 21/57 |
| 11,909,752 B1* | 2/2024 | Kapoor | | H04L 67/306 |
| 11,916,947 B2* | 2/2024 | Kapoor | | H04L 63/1425 |
| 11,922,328 B1* | 3/2024 | Gdak | | G06N 5/022 |
| 11,924,152 B2* | 3/2024 | Gao | | H04L 51/212 |
| 11,973,784 B1* | 4/2024 | Erlingsson | | G06F 9/5077 |
| 11,979,422 B1* | 5/2024 | Kapoor | | G06F 21/554 |
| 11,991,198 B1* | 5/2024 | Kapoor | | G06F 16/9038 |
| 12,002,465 B2* | 6/2024 | De | | G10L 15/22 |
| 12,007,870 B1* | 6/2024 | Jain | | G06F 11/3438 |
| 12,008,994 B2* | 6/2024 | De | | G10L 15/30 |
| 12,021,888 B1* | 6/2024 | Reed | | H04L 63/1425 |
| 12,034,754 B2* | 7/2024 | O'Hearn | | G06F 16/9038 |
| 12,058,160 B1* | 8/2024 | Erlingsson | | G06F 16/906 |
| 12,073,075 B2* | 8/2024 | Bhavaraju | | A61B 5/0022 |
| 12,079,643 B2* | 9/2024 | Ziraknejad | | G06F 40/295 |
| 12,086,275 B2* | 9/2024 | Goswami | | G06F 40/40 |
| 12,095,794 B1* | 9/2024 | Karaje | | H04L 67/306 |
| 12,095,796 B1* | 9/2024 | Godefroid | | G06F 9/542 |
| 12,095,879 B1* | 9/2024 | Erlingsson | | G06F 16/9038 |
| 2013/0191152 A1 | 7/2013 | Cremer et al. | | |
| 2015/0286802 A1 | 10/2015 | Kansara | | |
| 2018/0075219 A1* | 3/2018 | Klein | | G16H 20/70 |
| 2018/0173730 A1* | 6/2018 | Copenhaver | | G06F 16/212 |
| 2019/0005200 A1* | 1/2019 | Zimmerman | | G16H 50/30 |
| 2019/0149962 A1* | 5/2019 | Khaleghi | | G06F 40/284 |
| 2019/0220464 A1* | 7/2019 | Butani | | G06F 16/2455 |
| 2020/0065122 A1* | 2/2020 | Ziraknejad | | G06F 21/62 |
| 2020/0065307 A1* | 2/2020 | Roy | | G06F 16/24575 |
| 2020/0084595 A1* | 3/2020 | Khaleghi | | G16H 50/20 |
| 2020/0251111 A1* | 8/2020 | Temkin | | G06F 16/2423 |
| 2021/0058490 A1* | 2/2021 | Jain | | H04L 67/535 |
| 2021/0386964 A1* | 12/2021 | Youngblood | | A47C 27/085 |
| 2021/0406310 A1* | 12/2021 | Paulus | | G06F 16/24568 |
| 2022/0059228 A1* | 2/2022 | Chen | | G06F 16/254 |
| 2022/0114217 A1* | 4/2022 | Paulus | | G06F 16/24568 |
| 2022/0114346 A1* | 4/2022 | Galitsky | | G16H 50/20 |
| 2022/0179979 A1* | 6/2022 | Goswami | | H04L 63/0421 |
| 2022/0200869 A1* | 6/2022 | Erlingsson | | H04L 67/10 |
| 2022/0215101 A1* | 7/2022 | Rioux | | G06F 21/577 |
| 2022/0215948 A1* | 7/2022 | Bardot | | G16H 40/40 |
| 2022/0224707 A1* | 7/2022 | Kapoor | | G06F 16/9038 |
| 2022/0232024 A1* | 7/2022 | Kapoor | | G06F 21/57 |
| 2022/0232025 A1* | 7/2022 | Kapoor | | H04L 63/1425 |
| 2022/0247769 A1* | 8/2022 | Erlingsson | | G06F 9/5072 |
| 2022/0279004 A1* | 9/2022 | Erlingsson | | G06F 16/9038 |
| 2022/0293272 A1* | 9/2022 | Pang | | G16H 20/00 |
| 2022/0294816 A1* | 9/2022 | Martin | | H04L 67/535 |
| 2022/0303295 A1* | 9/2022 | Erlingsson | | G06F 16/9038 |
| 2022/0311794 A1* | 9/2022 | Maya | | G06F 11/0766 |
| 2022/0329616 A1* | 10/2022 | O'Hearn | | G06F 9/545 |
| 2022/0360600 A1* | 11/2022 | Reed | | G06F 16/9537 |
| 2022/0367056 A1* | 11/2022 | Lure | | G16H 40/67 |
| 2022/0369077 A1* | 11/2022 | Khaleghi | | G16H 40/67 |
| 2022/0382620 A1* | 12/2022 | Bramble | | G06F 11/0787 |
| 2022/0399112 A1* | 12/2022 | Bardot | | G16H 40/40 |
| 2022/0400129 A1* | 12/2022 | Kapoor | | G06F 16/9537 |
| 2022/0400130 A1* | 12/2022 | Kapoor | | H04L 63/10 |
| 2023/0029927 A1* | 2/2023 | Ziraknejad | | H04L 67/53 |
| 2023/0032686 A1* | 2/2023 | Williams | | G06F 16/9535 |
| 2023/0070255 A1* | 3/2023 | Paulus | | G06F 16/24568 |
| 2023/0075355 A1* | 3/2023 | Twigg | | H04L 67/306 |
| 2023/0214289 A1* | 7/2023 | Bramble | | G06F 11/0793 |
| 2023/0254330 A1* | 8/2023 | Singh | | G06F 11/323 |
| | | | | 726/23 |
| 2023/0275917 A1* | 8/2023 | Karmali | | G06F 16/9537 |
| | | | | 709/224 |
| 2023/0319092 A1* | 10/2023 | Zeng | | G06Q 10/06316 |
| | | | | 726/23 |
| 2023/0328086 A1* | 10/2023 | Kapoor | | H04L 63/1425 |
| 2023/0352169 A1* | 11/2023 | Whitmire | | G16H 10/60 |
| 2023/0386663 A1* | 11/2023 | Foody | | G16H 10/60 |
| 2023/0409636 A1* | 12/2023 | Paulus | | G06F 16/2282 |
| 2023/0420093 A1* | 12/2023 | Pandipati | | G16H 40/67 |
| 2024/0080329 A1* | 3/2024 | Reed | | G06F 16/9038 |
| 2024/0106846 A1* | 3/2024 | Kapoor | | H04L 63/10 |
| 2024/0143436 A1* | 5/2024 | Bramble | | G06F 11/0787 |
| 2024/0153634 A1* | 5/2024 | Ghosh | | G16H 50/20 |
| 2024/0154884 A1* | 5/2024 | Jain | | H04L 43/02 |
| 2024/0194354 A1* | 6/2024 | Shandilya | | G16H 50/70 |
| 2024/0212846 A1* | 6/2024 | Yusuf | | G16H 50/20 |
| 2024/0257930 A1* | 8/2024 | Jenudi | | G16H 50/20 |
| 2024/0257972 A1* | 8/2024 | Getz | | G16H 20/10 |
| 2024/0338577 A1* | 10/2024 | Gdak | | G06N 20/00 |

* cited by examiner

MANAGEMENT AND COORDINATION OF DATA FOR DIGITAL THERAPEUTICS TRIALS

BACKGROUND

Multiple databases may be used to store and collect data in accordance with a database schema, and may be used to facilitate storage and maintenance of organized data for a clinical trial testing the efficacy and safety of pharmaceuticals. Before a pharmaceutical can be approved by a regulatory agency, the pharmaceutical may undergo multiple clinical trials to test the efficacy and safety of the pharmaceutical, with regulations that, for example, provide privacy to the participants' personal health information (PHI) and personally identifiable information (PII) collected during the trial as well as control participants' enrollment in the trial and how the trial tests the desired endpoints. An endpoint may correspond to the outcome that is being measured by the clinical trial. A pharmaceutical drug, for example, might use survival as an endpoint, comparing the five-year survival rate using an experimental therapy against the five-year survival rate using another treatment or a placebo.

In clinical trials involving pharmaceuticals, such trials may have three phases: (1) the pre-trial phase; (2) the clinical trial phase, which involves administering a pharmaceutical, a medical device, etc.; and (3) the post-trial phase. During the pre-trial and post-trial phases, a clinical trial administrator may approach a participant with a mobile device (e.g., a tablet or laptop), and directly ask questions of the participant regarding the pharmaceutical. The administrator may manually enter the participant responses into a spreadsheet or data entry interface running on the mobile device. In some cases, the clinical trial administrator may communicate with the participant by telephone or video meeting and may alternatively use a desktop device to collect participant responses. The data collected from the participant responses in a trial (and the trial endpoint data) may be held in a clinical trial database called an electronic data capture (EDC).

SUMMARY

Presented herein are systems and methods for managing and coordinating data for digital therapeutics applications. In contrast to trials for pharmaceuticals, the types of data aggregated from trials of digital therapeutics applications may differ greatly from the types of data collected from clinical trials involving pharmaceuticals. A digital therapeutics may correspond to systems and devices implemented in software, hardware, firmware, program logic units, and any combination thereof, that can be used to cure, prevent, mitigate, or treat an array of diseases, disorders, and conditions. The trials for a digital therapeutics may operate differently than clinical trials involving pharmaceuticals in many ways. Notably, during the second phase (e.g., the clinical trial), there may be a participation phase using a digital interface for performing the digital therapeutic activities (alone or in combination with a pharmaceutical). There may be digital lessons or physical activities initiated periodically by the digital therapeutic as well as queries and responses required during the clinical trial. Thus, unique data may be electronically collected during the second phase that does not occur in traditional clinical trials.

To store and maintain the data for digital therapeutics trials, prior approaches may include a clinical database to manage data from the pre-trial phase and post-trial phase, and there is a separate application database to manage data from the trial phase. These two separate databases may not communicate with one another and are maintained by separate entities in separate locations. This may make it difficult to correlate digital therapeutics activity with endpoint data. For instance, a trial endpoint may be on a scale for engagement, and a participant may identify with a low engagement at the pre-trial phase. After performing the clinical trial using the digital therapeutic, however, the participant may identify as high engagement at the post-trial phase. Due to the lack of communication or interfacing among the databases for pre-trial, clinical trial, and post-trial data, it can be burdensome to match the participant with the same profile and conclude that the post-trial data shows that the digital therapeutic caused the increase in engagement.

Another disadvantage with prior approaches may be that because there are regulations (or other rules) for managing data collected during the three phases of a clinical trial, relying on separate databases requires additional effort to ensure each database complies with the corresponding regulations.

In addition, similar to clinical trials for pharmaceuticals or medical devices, prior approaches may involve a new database built for each new digital therapeutics trial that is evaluating a new digital therapeutic. For example, a new Electronic Data Capture (EDC), new identity verification, new informed consent, and a new entity hosting the EDC may be set up for each new trial. This may involve a substantial amount of time, effort, and cost, each time a new database is built for a new trial.

In such prior approaches, since new databases are created for each new digital therapeutic being evaluated, it may be difficult or impossible to integrate data across the various trials. Thus, more than one digital therapeutics trial may collect information in common, but this data must be duplicated for each database. This may cause unnecessary duplication of data both on the user device and on the servers operating the trials. Unnecessary excess memory and storage usage on the user device is required due to multiple mobile or web apps that the user may be forced to download and operate. Some older mobile devices may not have enough internal memory or storage to operate more than one trial at a time. Inefficiencies may occur because of the inability of data use and sharing among authorized users. Requiring a user to operate more than one mobile or web app can cause confusion because of inconsistent user experience (UX) across multiple mobile or web apps with different user interfaces.

To address these and other challenges, presented herein are systems and methods of managing access to data associated with trials for digital therapeutics on participants. A service may provide a shell to manage the data from all phases of the trial (e.g., pre-trial phase, clinical trial phase, and post-trial phase) in an integrated framework. The framework can be used for multiple digital therapeutics with minimal modification and thus allows for easy and rapid implementation, launch, and testing of a large quantity of multiple new digital therapeutics trials using the same plug-and-play shell. Each new digital therapeutic may be easily plugged in (e.g., plug-and-play) the same framework. One advantage may be the substantial time, effort, and cost that will be saved, from no longer having to build a new infrastructure for each new digital therapeutics trial. For example, the same Electronic Data Capture (EDC), identity verification, informed consent, and entity hosting the EDC can be used for multiple digital therapeutics trials. Regardless of the endpoints for each trial and the procedures involved running the trial, the use of a single framework for housing multiple trials can provide advantages of scale and efficiency.

The service herein may maintain a centralized site (e.g., data lake) where the data from all phases (e.g., pre-trial phase, trial phase, and post-trial phase) of the trial are stored and managed. The advantage in all three phases of the trial being coordinated for a participant in the same clinical trial data storage, may be that there is certainty that the data from a participant referred to in one phase of the trial will correlate to the data from the same participant in a different phase of the trial. For example, when there is data from the pre-trial phase that a participant has low engagement, then data from the post-trial phase that the same participant now has high engagement. Since the data is stored in the same data storage as the data from the trial phase, it can be easily concluded that the digital therapeutic caused the positive increase in engagement.

A centralized data storage makes this correlation much easier to make. Since the participant responses during the trial phase help determine whether the digital therapeutic is the reason for the clinical trial results, it may be useful to maintain the data in a centralized manner. Even when considering multiple digital therapeutics trials, there may be a benefit in that data can be pulled from the same location to coordinate multiple trials involving the same participant.

Furthermore, it may be advantageous to use a common framework, as described herein, on the user device so that the user (e.g., a clinician) is able to view a single user interface and can launch multiple digital therapeutics trials from one place. For example, multiple digital therapeutics trials can be integrated when their mobile application code and API (application program interface) code is harmonized with pre-defined criteria corresponding to the framework interface. In addition, a user may manage multiple digital therapeutics trials within the framework that are administered or sponsored by different organizations having different site staff. In this case, the site staff may have access only to data for the digital therapeutics trial that they own or coordinate in the clinical trial data storage.

The service herein may manage a closed system in which digital therapeutics user data, the clinical endpoint, and a clinical data manager are all associated with a single user ID and sent to the same centralized data storage. This type of closed system may improve data security and integrity, relative to approaches relying on a multiplicity of different databases. Additionally, the mobile or web app may be executed on a single platform in which multiple digital therapeutics treatments can be delivered, therefore making the solution scalable across many sites and for many digital therapeutics treatments, including third-party treatments.

Aspects of the present disclosure are directed to a method and a system for managing access to data associated with trials for digital therapeutics on subjects. A server can maintain a data storage for a plurality of phases associated with a trial for a digital therapeutic on a plurality of participants. The data storage may include (i) a first portion of a plurality of datasets from the plurality of participants from one or more of the plurality of phases of the trial, and (ii) a second portion of the plurality of datasets from the digital therapeutics in at least one of the plurality of phases of the trial. The server can receive from a user device, a request identifying a phase of the plurality of phases for which the plurality of datasets is to be accessed. The server can select a corresponding portion of the plurality of datasets based on the phase identified in the request. The server can provide the user device access to the corresponding portion of the plurality of datasets in the data storage.

In some embodiments, the server may receive from the user device, a second request to define a plurality of parameters for the trial, the plurality of parameters identifying at least one of: the digital therapeutics, the plurality of phases, and a respective endpoint for each of the plurality of phases. The server may establish the data storage in a data lake in accordance with the plurality of parameters for the trial. In some embodiments, the server may identify a plurality of trials associated with a corresponding plurality of conditions of the plurality of participants provided with the digital therapeutics, and establish a plurality of data storages for the corresponding plurality of trials.

In some embodiments, the server may receive, from the user device, a second request to associate the data storage with a second data storage. The second data storage may include a second plurality of datasets from a second trial separate from the trial associated with the data storage. The server may link, responsive to the second request, the second data storage with the data storage to provide the user device access to the data storage and the second data storage. In some embodiments, the server may identify from a plurality of access privileges, an access privilege for a user associated with the user device, wherein providing the access further includes providing the user device access to the portion of the plurality of datasets, responsive to the access privilege defining that the user is permitted to access the portion.

In some embodiments, wherein receiving the request further includes receiving the request identifying a questionnaire to add to the phase of the plurality of phases, the server may generate, at least one dataset identifying the questionnaire to add to corresponding portion of the plurality of datasets. In some embodiments, wherein maintaining the data storage further includes removing, from the data storage, a first dataset in one portion of the plurality of datasets corresponding to a second dataset in another portion of the plurality of datasets.

In some embodiments, receiving the request further includes receiving the request identifying a participant of the plurality of participants for which the plurality of datasets is to be accessed, wherein providing the access further includes correlating, within the plurality of datasets on the data storage, one or more datasets associated with the participant identified in the request. In some embodiments, at least one of the plurality of datasets may be generated using at least one of electronic data capture (EDC), identity verification, and informed consent. In some embodiments, at least one of the plurality of participants may be administered with a pharmaceutical to address a condition, at least partially concurrently with use of the digital therapeutics.

BRIEF DESCRIPTION OF THE DRAWINGS

The foregoing and other objects, aspects, features, and advantages of the disclosure will become more apparent and better understood by referring to the following description taken in conjunction with the accompanying drawings, in which.

DETAILED DESCRIPTION

For purposes of reading the description of the various embodiments below, the following enumeration of the sections of the specification and their respective contents may be helpful:
  Section A describes systems and methods for managing and coordinate data for digital therapeutics trials; and
  Section B describes a network and computing environment, which may be useful for practicing embodiments described herein.

Figure 1:
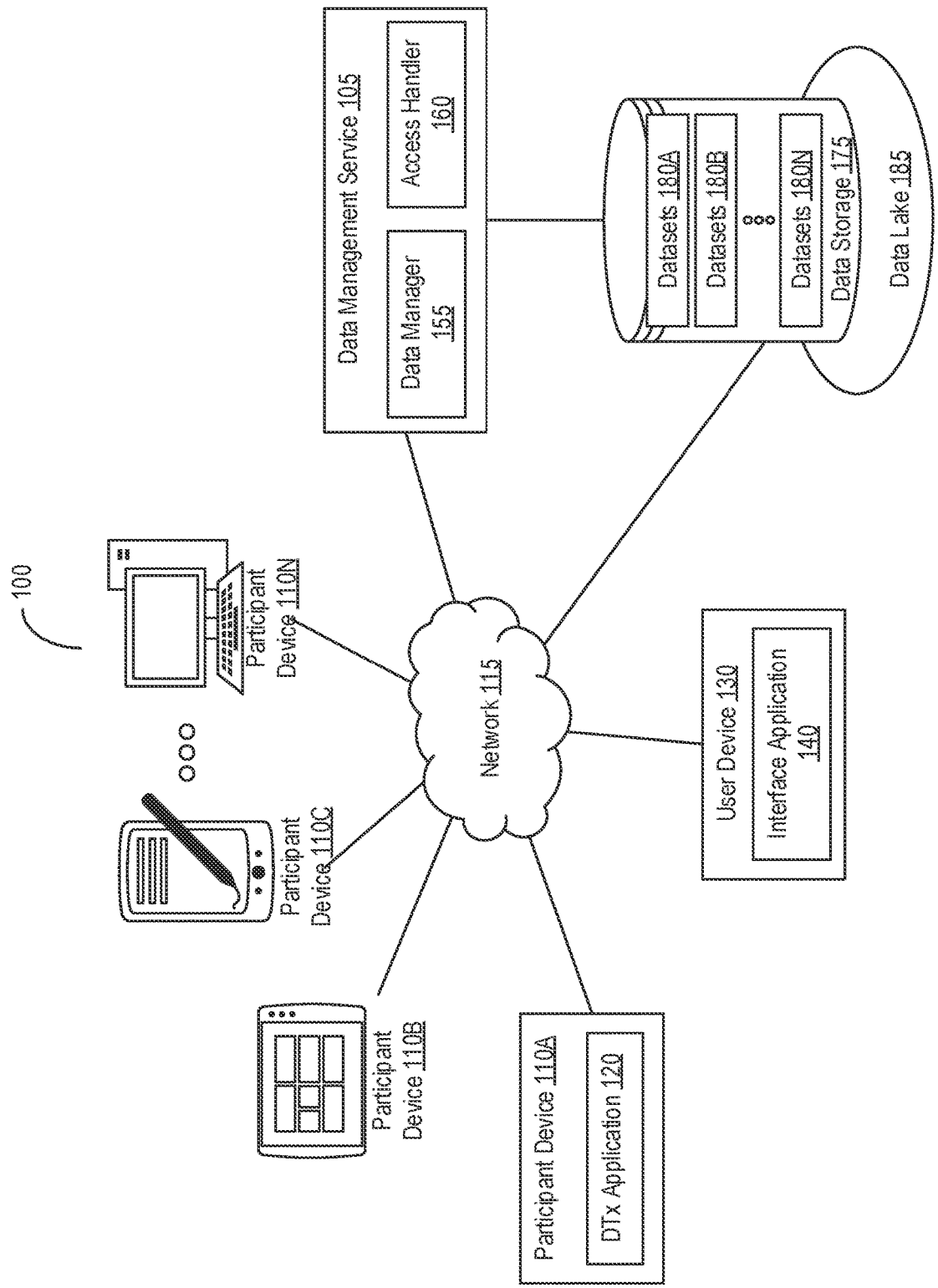
FIG. 1 depicts a block diagram of a system for managing and coordinating data in accordance with an illustrative embodiment.

A. Systems and Methods for Managing and Coordinating Data for Digital Therapeutics Trials Referring now to FIG. 1, depicted is a block diagram of a system 100 for managing and coordinating data. In an overview, the system 100 may include at least one data management service 105, at least one user device 130, and a set of participant devices 110A-N (hereinafter generally referred to as participant devices 110), communicatively coupled with one another via at least one network 115. At least one participant device 110 (e.g., the first participant device 110A as depicted) may include at least one digital therapeutics application 120. The user device 130 may include at least one interface application 140 (sometimes herein referred to as a data management application or portal application). The data management service 105 may include at least one data manager 155 and at least one access handler 160, among others. The data management service 105 may include or have access to a data storage 175. The data storage 175 may store, maintain, or otherwise include one or more datasets 180A-N (hereinafter generally referred to as datasets 180) among others. The data storage 175 may form or may be part of a data lake 185. In some embodiments, the functionality of the digital therapeutics application 120 and the functionality of the interface application 140 may be performed in part on the data management service 105.

In further detail, the data management service 105 may (sometimes herein generally referred to as a computing system or a service) be any computing device comprising one or more processors coupled with memory and software and capable of performing the various processes and tasks described herein. The data management service 105 may be in communication with the one or more participant devices 110 and the data storage 175 via the network 115. The data management service 105 may be situated, located, or otherwise associated with at least one server group. The server group may correspond to a data center, a branch office, or a site at which one or more servers corresponding to the data management service 105 is situated.

Within the data management service 105, the data manager 155 may manage data associated with data that is stored or to be stored in the data storage 175. The data manager 155 may execute, initiate, or receive data from the digital therapeutics application 120 or the participant device 110. The data manager 155 may execute, initiate, or receive data from the interface application 140 or the user device 130. The data manager 155 may communicate the data stored in the data storage 175 to any of the participant device 110 or the user device 130. For example, the data manager 155 may receive data from the participant device 110A, and may store the data in the data storage 175. In addition, the data manager 155 may retrieve data from the data storage 175, and may send the data to the user device 130. In some embodiments, the data manager 155 may send/receive data based at least on an indication from the access handler 160.

Within the data management service 105, the access handler 160 may control access to data that is stored or to be stored in the data storage 175. The access handler 160 may identify or verify the user device 130 to determine whether to provide access to data to the user device 130. Upon a determination that the user device 130 may be granted the access, the access handler 160 can provide the access to the user device 130. Upon a determination that the user device 130 should not be granted the access, the access handler 160 can deny a request for the access. For example, the access handler 160 can identify or verify the user device 130 based on identification information of the user device 130.

The participant device 110 may be any computing device comprising one or more processors coupled with memory and software and capable of performing the various processes and tasks described herein. The participant device 110 may be operated by a participant (sometimes herein referred to as a subject, patient, or user). The participant device 110 may be in communication with the data management service 105 and the data storage 175 via the network 115. The participant device 110 may be a smartphone, other mobile phone, tablet computer, wearable computing device (e.g., smart watch, eyeglasses), or laptop computer. The participant device 110 may be used to access the digital therapeutics application 120. In some embodiments, the digital therapeutics application 120 may be downloaded and installed on the participant device 110 (e.g., via a digital distribution platform). In some embodiments, the digital therapeutics application 120 may be a web application with resources accessible via the network 115.

The digital therapeutics application 120 executing on the participant device 110 may provide a digital therapeutics, and may facilitate a session (sometimes referred to herein as a therapy session) to address at least one condition of the user. The condition of the user may include, for example, a chronic pain (e.g., associated with or include arthritis, migraine, fibromyalgia, back pain, Lyme disease, endometriosis, repetitive stress injuries, irritable bowel syndrome, inflammatory bowel disease, and cancer pain), a skin pathology (e.g., atopic dermatitis, psoriasis, dermatillomania, and eczema), a cognitive impairment (e.g., mild cognitive impairment (MCI), Alzheimer's, multiple sclerosis, and schizophrenia), and other ailments (e.g., narcolepsy and oncology), among others.

The user may be at least partially concurrently taking a pharmaceutical (sometimes referred herein as a medication or drug) to address the condition, while being provided sessions through digital therapeutics application 120. For instance, if the medication is for pain, the user may be taking acetaminophen; a nonsteroidal anti-inflammatory composition; an antidepressant, an anticonvulsant; or other composition, among others. For skin pathologies, the user may be taking a steroid, antihistamine, or topical antiseptic, among others. For cognitive impairments, the user may be taking cholinesterase inhibitors or memantine, among others. For narcolepsy, the user may be taking a stimulant or antidepressant, among others. The user of the digital therapeutics application 120 may also participate in other psychotherapies for these conditions.

The digital therapeutics application 120 can include, present, or otherwise provide a user interface including one or more UI elements to a participant via the participant device 110 in accordance with a configuration on the digital therapeutics application 120. The UI elements may correspond to visual components of the user interface, such as a command button, a text box, a check box, a radio button, a menu item, and a slider, among others. In some embodiments, the digital therapeutics application 120 may provide a session (sometimes referred to herein as a therapy session) via the user interface to achieve a behavioral endpoint of the participant (sometimes herein referred to as a patient, person, user, or subject). A behavioral endpoint can be, for example, a completion of the session, a physical or mental goal of a participant, a completion of a medication regimen, or a behavioral endpoint indicated by a doctor. A participant may be an individual who participates in the clinical trial. A participant may be enrolled in and participating in a digital therapeutics trial using the digital therapeutics application 120 on the participant device 110.

The user device 130 (sometimes herein referred to as an end user computing device) may be any computing device comprising one or more processors coupled with memory and software and capable of performing the various processes and tasks described herein. The user device 130 may be in communication with the data management service 105 and the data storage 175 via the network 115. The user device 130 may be a smartphone, other mobile phone, tablet computer, wearable computing device (e.g., smart watch, eyeglasses), or laptop computer. The user device 130 may be used to run the interface application 140 to interface with the data management service 105 to access data on the data storage 175. In some embodiments, the interface application 140 may be downloaded and installed on the user device 130 (e.g., via a digital distribution platform). In some embodiments, the interface application 140 may be a web application with resources accessible via the network 115.

A number of different types of users may operate the interface application 140 executing on the user device 130. A user may include any individual who accesses the data management service 105 and can be, for example, a trial coordinator, data manager, maintenance engineer/programmer, or other sponsor representative. A sponsor may be a research sponsor, developer of a digital therapeutics, backer of the research, or owner or lead responsible for research conduct and may be responsible for trial management, trial design, and regulatory interactions. A sponsor may access the data management service 105 for creating and managing the trial(s) and evaluating the endpoint data.

In addition, there may be other entities or individuals associated with the trials and entry of data via the interface application 140. For instance, a clinical trial coordinator may be an individual who executes the research trial and collects data for entry through the data management service 105 via the interface application 140. The clinical trial coordinator may interact directly with research participants. A trial coordinator may access the data management service 105 for approving or rejecting a participant's enrollment and selecting endpoint thresholds or other trial criteria. A principal investigator may be an individual who is responsible for compliant execution of the trial; attributable, legible, contemporaneous, original, and accurate (ALCOA) data collection; and Good Clinical Practice (GCP) compliance. The principal investigator may interact directly with research participants. A principal investigator may access the data management service 105 for assessing compliance to enrollment criteria and compliance with data security of PII and PHI.

Furthermore, site staff may refer to the principal investigator, clinical trial coordinator, or other individuals responsible for research participant management. Site staff may access the data management service 105 to use participant contact information for participant ID verification and enrollment. This identifying information is used to verify the identity of the participant and is accessible only to site staff responsible for the trial administration and participant interaction and communication. Records of participant informed consent are included in this information. The clinical trial database manager may be responsible for building and validating a clinical trial database. The data manager may also be responsible for addressing issues and issuing queries to principal investigators if necessary. The data manager may access the data management service 105 for defining access control mechanisms for data, for instance, by assigning roles to individuals, where the role corresponds to an access level for various data types.

The data storage 175 may store and maintain various resources and datasets 180 associated with the data management service 105 and the digital therapeutics application 120. In some embodiments, the data storage 175 may be part of, may form, or may otherwise be the data lake 185. The data lake 185 may be a repository to store and maintain the data in both structured and unstructured formats. The data lake 185 may be used to store one or more data storages 175 storing datasets 180 from one or more trials. The data lake 185 may correspond to or include one or more storages (e.g., distributed system or cloud storage) for maintaining data in an unstructured or structured format. In some embodiments, the data storage 175 may include a database management system (DBMS) to arrange and organize at least a portion of the data maintained thereon. The data storage 175 may be in communication with the data management service 105 and the one or more participant devices 110 via the network 115. While running various operations, the data management service 105 and the digital therapeutics application 120 may access the data storage 175 to retrieve identified data therefrom. The data management service 105 and the digital therapeutics application 120 may also write data onto the data storage 175 from running such operations.

The datasets 180 stored and maintained on the data storage 175 may be aggregated from participants (e.g., directly or indirectly through a clinical trial site staff) and from the digital therapeutics application 120. One type of datasets 180 may include digital therapeutics user data, such as data about a user's interaction with activities or a user's engagement with the digital therapeutics. This may be analogous to sites in pharmaceutical clinical trials monitoring adherence to the pharmaceutical. Another type of datasets 180 collected may include Electronic Patient Reported Outcome (ePRO). ePRO may include clinical outcome assessments self-reported by participants, generally via a validated questionnaire.

Continuing on, another type of datasets 180 may include trial data that is entered by the participant (e.g., demographic data, eligibility questionnaires, etc.). This information may include validated clinical scales (C-SSRS, PHQ-9, etc.) or created forms and questionnaires (demographics, etc.). Another type of datasets 180 collected may include application metadata or application usage data collected automatically from the digital therapeutics data 120. Specific data collected may be defined and configured by a data manager using tools or functions in a clinical trial facilitation framework.

Figure 2:
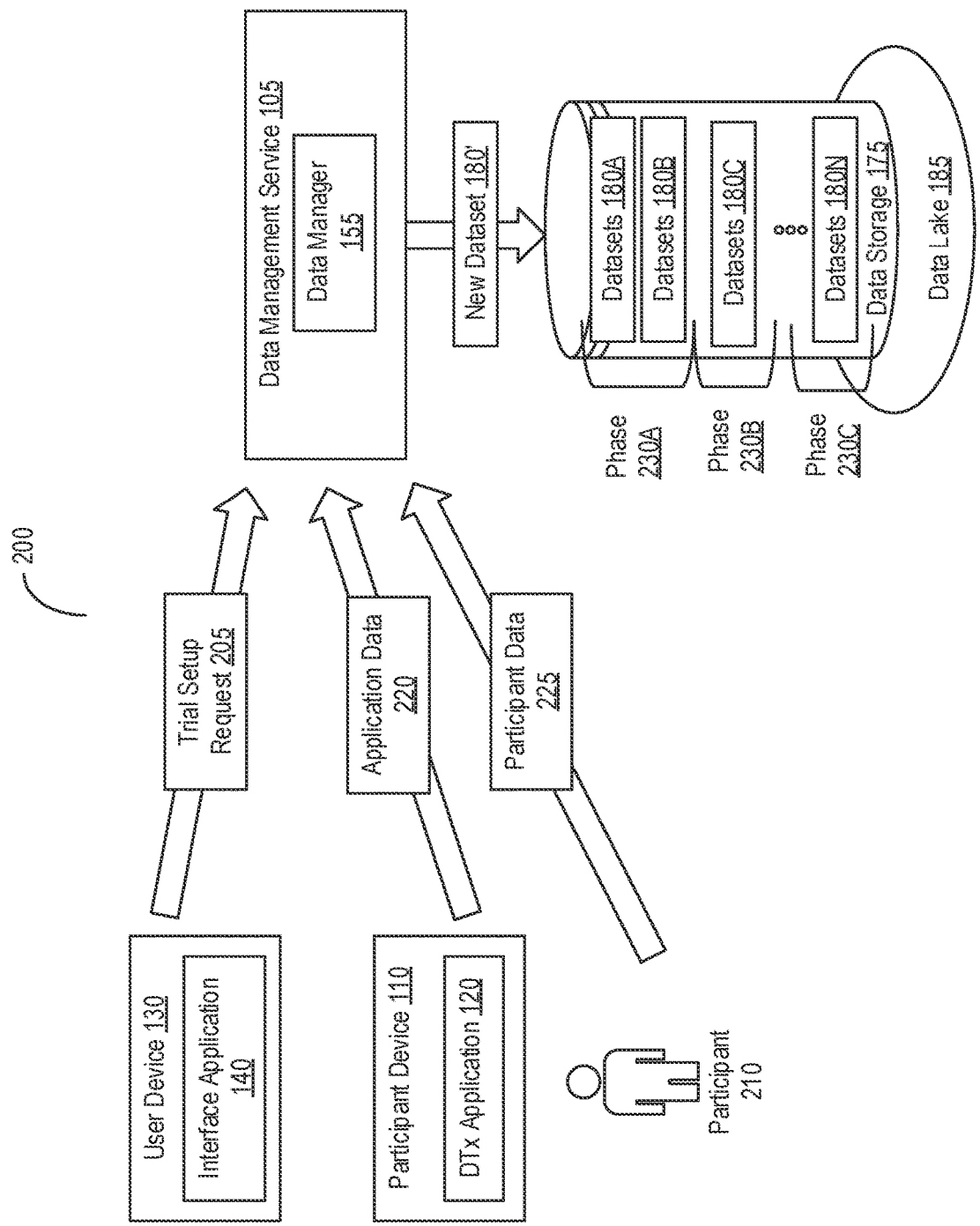
FIG. 2 depicts a block diagram of a system for managing and coordinating data in accordance with an illustrative embodiment.

Referring now to FIG. 2, depicted is a block diagram of a process 200 for managing data in the system 100 for managing and coordinating data. The process 200 may correspond to or include operations in the system 100 to manage datasets 180 on the data storage 175. Under the process 200, the interface application 140 executing on the user device 130 may transmit or send at least one trial setup request 205 to the data management service 105. The trial setup request 205 may include a set of parameters to define one or more trials for digital therapeutics. The set of parameters may be defined by a user (e.g., clinical trial coordinator, site staff, or clinical trial manager) of the interface application 140. The set of parameters of the trial setup request 205 may identify or include digital therapeutics information (e.g., an identifier for the digital therapeutics application 120), a set of participants 210 to use the digital therapeutics (e.g., anonymized identifiers or segment identifier), one or more phases 230A-N (hereinafter generally referred to as phases 230) (e.g., pre-trial phase, clinical trial phase, and post-trial phase), and a respective endpoint (e.g., behavioral, psychological, or mental) for each phase via the digital therapeutics, among others.

In some embodiments, the parameters of the trial setup request 205 may identify or include a set of questionnaires to provide the participants 210 for at least one phase 230 of the trial of the digital therapeutic. For example, the trial setup request 205 may include an upfront questionnaire, a lesson, instruction, biomarkers to be measured, a post-trial questionnaire, or otherwise any information for setting up a trial or for determining a status of the participant during the trial. In some embodiments, the trial setup request 205 may identify users (e.g., a clinical trial site staff) of the interface application 140 and a list of access privileges for each user for data associated with the trial. The access privilege may specify which type of data each user of the interface application 140 can access (e.g., read, write, or edit).

The data manager 155 executing on the data management service 105 may receive, retrieve, or otherwise identify the trial setup request 205 from the user device 130. The data manager 155 may parse the trial setup request 205 to identify information associated with trials for digital therapeutics. From parsing, the data manager 155 may identify the digital therapeutics application 120 to be tested for efficacy, safety, and performance on the participants 210 for the phases 230 of the trial. In some embodiments, the data manager 155 may identify a set of digital therapeutics applications 120 from the trial setup request 205. The set of digital therapeutics applications 120 may be for different conditions (e.g., chronic pain, skin pathology, or multiple sclerosis). In some embodiments, the set of the digital therapeutics applications 120 may be for a single type of application used for different conditions or several different types of applications for the respective conditions.

In some embodiments, the data manager 155 may identify a set of participants 210 to be included in the trial from the trial setup request 205. The set of participants 210 may include users of the digital therapeutics applications 120. Each of the participants 210 may be identified using an anonymized identifier. For example, the identifier may correspond to an account identifier for logging into the digital therapeutics application 120 or a randomly generated name used by a clinical trial site staff to uniquely reference the participant 210. In some embodiments, the data manager 155 may identify the users (e.g., a clinical trial site staff) of the interface application 140 and the list of access privileges for each user from the digital therapeutics application 140. In some embodiments, the data manager 155 may identify the set of questionnaires to provide the participants 210 for at least one phase 230 of the trial of the digital therapeutic treatment.

In some embodiments, the data manager 155 may identify a set of trials from the trial setup request 205. Each trial may define or include a set of phases 230 (sometimes herein referred to as stages), such as a pre-trial phase, a clinical trial phase to test the digital therapeutics application 120, and a post-trial phase, among others. The set of trials may be for different conditions of participants 210 using the digital therapeutics application 120 to be tested for at least one of efficacy, safety, or performance on the participants 210. The set of trials for different conditions may include, for example, chronic pain, a skin pathology, a cognitive impairment, and other ailments, among others. The set of trials for different conditions may include one or more pharmaceutical conditions. The set of trials for different conditions may be for a set of groups with different severity of a single condition.

With the identifications, the data manager 155 may initialize, configure, and establish one data storage 175 in accordance with the parameters for the trial. The data storage 175 may be used to store data across phases 230 of a given trial for one or more digital therapeutics (e.g., one or more digital therapeutics applications 120). For each trial, the data manager 155 may instantiate or establish a respective data storage 175 to store one or more datasets 180 for the trial. For instance, the data manager 155 may create a first data storage 175 for a trial testing the efficacy of a digital therapeutic and a second data storage 175 for a trial testing the safety of the digital therapeutics. Each trial may have three phases 230, such as a pre-trial, a clinical trial, and a post-trial phase. The data storage 175 may be established in or to form the data lake 185. In some embodiments, the data storage 175 may correspond to the datasets 180 corresponding to a given trial within the data lake 185. In some embodiments, the data storage 175 may correspond to or define a portion of the data lake 185 in which the datasets 180 for a given trial across one or more phases 230 is to be stored and maintained.

With the establishment, the data manager 155 may manage, administer, or otherwise maintain the data storage 175 for the set of phases 230 (e.g., a pre-trial, clinical trial, and post-trial) associated with the trial of the digital therapeutics on the participants 210. The data storage 175 may include a set of datasets 180. The set of datasets 180 may be associated with one or more phases 230 of the trial for the digital therapeutics. At least one portion of datasets 180 may be from the participants 210 partaking in a corresponding phase 230 of the trial. For instance, the datasets 180 for the pre-trial phase 230A or a post-trial phase 230C may be acquired from answers to questionnaires by participants 210. The questionnaires may be provided to the participants 210 directly via a prompt (e.g., on the digital therapeutics application 120 or another application) or via a clinician site staff (e.g., using the interface application 140 to enter data). At least one portion of datasets 180 may be from the digital therapeutics in a corresponding phase 230 of the trial. The data may be obtained or received from the digital therapeutics application 120 during the clinical trial phase 230B, and may include, for example, metadata or log data identifying interactions by the participants 210 with the digital therapeutics application 120 running on the participant device 110.

In maintaining, the data manager 155 may retrieve, identify, or otherwise receive application data 220 from the digital therapeutics application 120. The application data 220 may identify or include information generated by the digital therapeutics application 120 running on the participant device 110. For example, the application data 220 may include: log data identifying one or more interactions by the participant 210 with the digital therapeutics application 120 or events triggered by processes while running the digital therapeutics application 120; a completion level for the participant 210 through the lessons provided by the digital therapeutics application 120; a performance score of the participant 210 in carrying out tasks as directed through the lessons; physiological measurements of the participant 210 while using the digital therapeutics application 120; and metadata associated with the digital therapeutics application 120 (e.g., version identifier, network address, geographic data, device identifier, anonymized identifier, and target condition to be addressed) or identifying which phase 230 the application data 220 is obtained, among others. The application data 220 may be retrieved during at least one of the phases 230 (e.g., the clinical trial phase 230B) of the trial.

In conjunction, the data manager 155 may retrieve, identify, or otherwise receive participant data 225 from the participant 210. The participant data 225 may be received via the digital therapeutics application 120, the interface application 140, or another application operated by clinical trial site staff, among others. In some embodiments, the participant data 225 may be sent to the data management service 105 without using the participant device 110. For example, the participant 210 may directly communicate with a doctor or a clinician, who then may input or request to store the communicated information in the data management service 105 or in the data storage 175.

The participant data 225 may include or identify information about the participant 210 acquired outside the digital therapeutics application 120. For example, the participant data 225 may identify or include one or more responses to a questionnaire; one or more traits of the participant 210 (e.g., age, race, gender, geographic location, or demographics); a condition of the participant 210 to be addressed via the digital therapeutics application 120; a severity of the condition in the participant 210; various physiological measurements taken from the participant 210 by a clinical trial site staff; diagnosis or evaluation information inputted by a clinician (e.g., a doctor or nurse) regarding the participant 210; data directly from the participant 210 (e.g., electronic patient-reported outcomes (ePRO)); and metadata identifying which phase 230 the participant data 225 is obtained, among others. In some embodiments, the participant data 225 may be generated in accordance with electronic data capture (EDC), new identity verification for the participant 210, and informed consent on the part of the participant 210. The participant data 225 may be retrieved during at least one of the phases 230 (e.g., the pre-trial phase 230A or post-trial phase 230C) of the trial.

With the receipt of the new data (e.g., the application data 220 or participant data 225), the data manager 155 may create, write, or otherwise generate at least one new dataset 180' to store onto the data storage 175. Using the new data, the data manager 155 may generate the new dataset 180' to include the information included therein. The data manager 155 may parse the newly received data to identify which phase 230 in the trial the data is associated with. With the identification of the phase 239, the data manager 155 may store or include the new dataset 180' with the portion of the datasets 180 corresponding to the phase 230. For example, the data manager 155 may update the portion of the datasets 180 corresponding to the first phase 230A when the newly received data (e.g., the application data 220 or the participant data 225) is identified as associated with the first phase 230A.

In some embodiments, the data manager 155 may generate the dataset 180' or configure at least a portion of the data storage 175, using electronic data capture, identity verification, and informed consent for participant data 225. The data manager 155 may generate a shell or framework that can be used for various types of trials, phases, or digital therapeutics applications. In some embodiments, regardless of endpoints for each trial and procedures involved running the trials, the data manager 155 may provide a single framework for housing multiple trials. In some embodiments, the data manager 155 or created shells or frameworks are configured to capture specific clinical data from the participant devices 110 (e.g., ePRO data, app metadata, authentication data records, audit trail records, participant identification, and informed consent, etc.). The captured data may be provided to the user device 130 (e.g., the response 310, as discussed below in greater detail).

In conjunction, the data manager 155 may de-duplicate the datasets 180 across the phases 230 on the data storage 175. The data manager 155 may identify the duplicated information in the dataset 180 in one portion (e.g., associated with the phase 230A) and the dataset 180 in another portion (e.g., associated with the phase 230B). With the identification, the data manager 155 may remove the duplicated information from at least one of the identified datasets 180. For example, when the data manager 155 identifies both the datasets 180A and the datasets 180B include duplicated data associated with the phases 230A and 230B respectively, the data manager 155 may determine to remove the duplicated data from the datasets 180B. In this example, both the datasets 180A and 180B may identify demographic information for the same participant 210, and the data manager 155 may reduce the instances of the same demographic information by removing the data from one of the datasets 180A or 180B.

In some embodiments, the data manager 155 may associate or link multiple data storages 175 from multiple trials to provide the interface application 140 access to the linked set of data storages 175 (or portions of datasets 180 across different data storages 175). The data management service 105 may provide for plug-and-play functionality of the data storages 175 from multiple trials. For instance, the plug-and-play functionality may allow linkage or association of a first data storage 175 containing datasets 180 for a trial to test a safety of a digital therapeutic, with a second storage 175 containing datasets 180 for a trial to test an efficacy of the digital therapeutic. In some embodiments, the data manager 155 may retrieve, identify, or receive a request to link one data storage 175 from one trial with another data storage 175 from another trial from the interface application 140. The request to link may be a part of the trial setup request 205, and may identify the data storages 175 corresponding to different trials to be linked. In some embodiments, the request may identify the portions of datasets 180 from the different trials stored on corresponding data storages 175 to be linked.

Upon receipt, the data manager 155 may determine, select, or otherwise identify the data storages 175 from multiple trials to be linked as identified in the request. In some embodiments, the data manager 155 may identify portions of datasets 180 across multiple data storages 175 from multiple trials to be linked as defined in the request. With the identification, the data manager 155 may link or associate the data storages 175 from multiple trials. In some embodiments, the data manager 155 may link the portions of datasets 180 across multiple data storages 175 from multiple trials. The data manager 155 may aggregate, join, or otherwise combine the data storages 175 from multiple trials in order to link them. The data manager 155 may assign the portions of datasets 180 identified in the requests to the data storages 180 from multiple trials of one another. To assign, the data manager 155 may generate an identifier to indicate that the portions of dataset 180 are associated with the multiple data storages 175 from multiple trials. With the linking of the multiple data storages 175 from multiple trials, the data manager 155 may enable or provide the user of the interface application 140 access to the linked data storages 175 from multiple trials with a single query or request.

Figure 3:
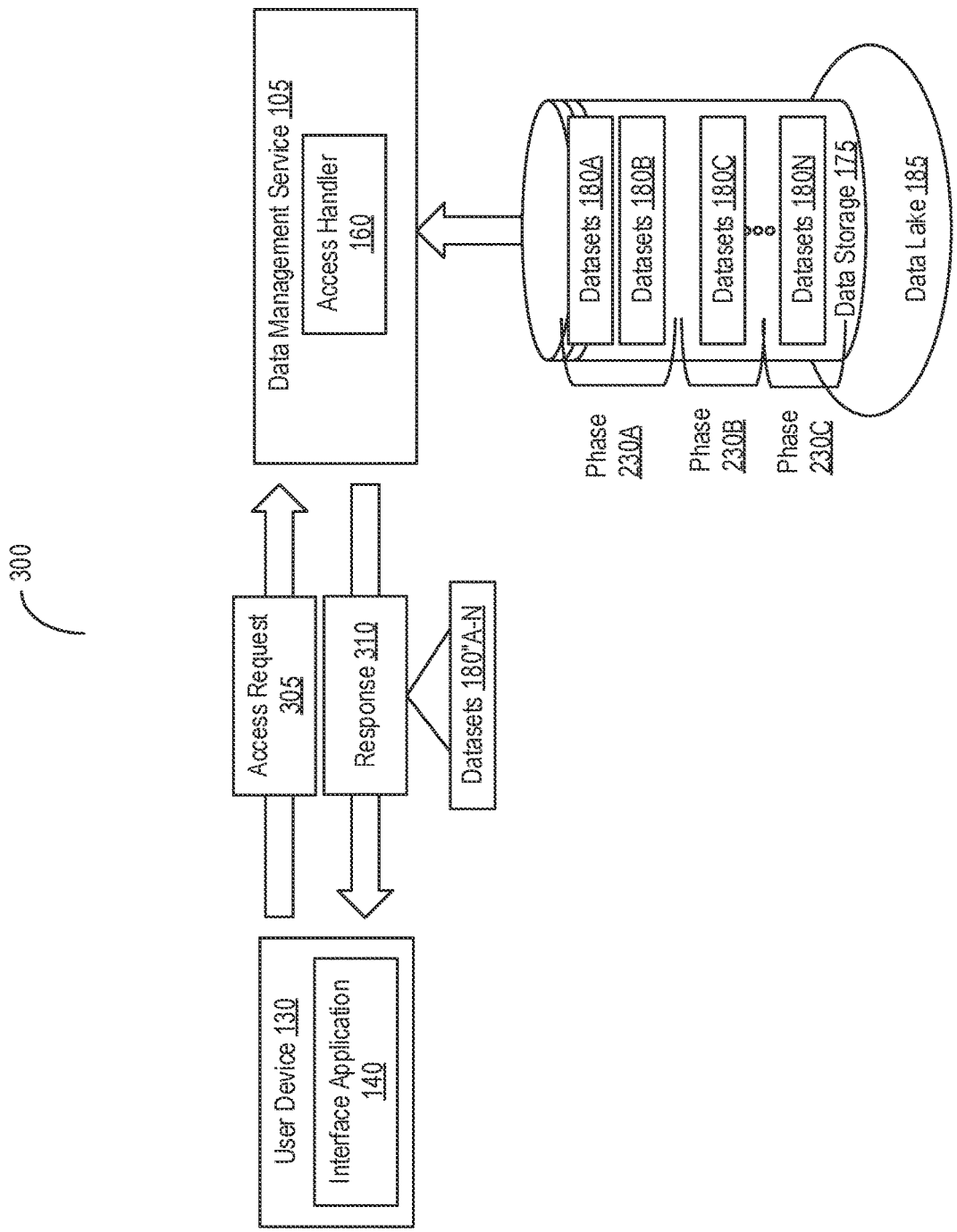
FIG. 3 depicts a block diagram of a system for accessing data in accordance with an illustrative embodiment.

Referring now to FIG. 3, depicted is a block diagram of a process 300 for accessing data in the system 100. The process 300 may correspond to or include operations in the system 100 to access data on the data storage 175. Under process 300, the interface application 140 on the user device 130 may transmit or send an access request 305 to the data management service 105. The access request 305 may be to query for datasets 180 stored on the data storage 175 for viewing or editing, or to store new data onto the data storage 175. The access request 305 may include or identify one or more constraints for identifying one or more portions of the datasets 180 stored on the data storage 175 to be accessed.

In some embodiments, the access request 305 may include or identify the phase 230 of the trial for which the datasets 180 on the data storage 175 are to be accessed. For example, the access request 305 may identify a pre-trial phase 230A, a clinical phase 230B, or a post-trial phase 230C, for which associated datasets 180 are to be accessed. In some embodiments, the access request 305 may include or identify one or more participants 210 (e.g., using anonymized identifiers, traits, or other characteristics) for which the datasets 180 are to be accessed. For instance, the access request 305 may identify a particular participant 210 or a cohort of participants 210, for which associated datasets 180 are to be accessed. In some embodiments, the access request 305 may include or identify a particular digital therapeutic application 120 for which datasets 180 are to be accessed. In some embodiments, the access request 305 may include or identify a particular condition for which datasets 180 are to be accessed. The requested datasets 180 may be stored or maintained on one data storage 175 that is a data lake.

The access request 305 may identify or include other information in connection with accessing the datasets 180. The access request 305 may also identify a type of operation to be performed on the datasets 180, such as read, write, view, or create, among others. In some embodiments, the access request 305 may include new data to be stored or entered onto the data storage 175, similar to the application data 220, participant data 225, or trial setup request 205 (e.g., at least one questionnaire). For example, the access request 305 may include a list of questionnaires to measure the safety, efficacy, or performance of the digital therapeutics application 120 to be provided to the participants of a given trial. In some embodiments, the access request 305 may include or identify information indicating an identification of a clinician, clinic, or user device based on which the access handler 160 may determine whether to provide the access. For example, the access request 305 may include a registration number of a clinician, clinic, or user device that requests the access.

The access handler 160 executing on the data management service 105 may retrieve, identify, or otherwise receive the access request 305 from the interface application 140 on the user device 130. Upon receipt, the access handler 160 may parse the access request 305 to extract or identify the one or more constraints identified therein for finding a corresponding portion of dataset 180". Based on the constraint, the access handler 160 may identify or select a corresponding portion of the datasets 180" on the data storage 175. In some embodiments, the access handler 160 may identify or select the portion of datasets 180" corresponding to the phase 230 identified in the access request 305. In some embodiments, the access handler 160 may select the portion of datasets 180" corresponding to the digital therapeutics application 120 identified in the access request 305. In some embodiments, the access handler 160 may select the portion of datasets 180" corresponding to the particular condition tested in the trial identified in the access request 305.

In some embodiments, the access handler 160 may select the portion of datasets 180" corresponding to the participants identified in the access request 305. The access handler 160 may associate, map, or otherwise correlate datasets 180 from the different portions (or phases 230) for the identified participant 210. For example, the access handler 160 may identify the datasets 180 in each portion (or phase 230) associated with the participant 210. The datasets 180 may be taken from the application data 220 generated when the participant 210 used the digital therapeutics application 120. The datasets 180 may also be obtained from the participant data 225 obtained via questionnaire presented by a clinical trial site staff. With the identifications, the access handler 160 may correlate the datasets 180 as associated with the same participant 210.

In some embodiments, the access handler 160 may determine whether to grant or permit access to the user device 130 to the selected portion of the datasets 180" in the data storage 175 in accordance with access privileges for the user. The access privileges may be defined for the user of the device 130 in the trial setup request 205 used to establish the data storage 175, and may specify which types of operations the user is permitted (e.g., read, write, view, or create). The access handler 160 may identify the access privilege for the user as defined in establishment of the data storage 175. With the identification, the access handler 160 may determine whether the user device 130 is to be permitted access to the portion of the datasets 180". The determination may be on a per dataset 180" basis. When the access privilege permits access, the access handler 160 may determine to grant the user device 130 access to the selected portion of the datasets 180" for the permitted types of operations. Otherwise, when the access privilege denies access, the access handler 160 may determine to restrict or deny the user device 130 access to the selected portion of the datasets 180" for the unpermitted types of operations.

In some embodiments, the access handler 160 may control or regulate access to datasets 180" based on authentication information from the user device 130. The access handler 160 may identify authentication information from the access request 305. For example, the authentication information may include a user identifier and password for the user of the user device 130, among others. In some embodiments, the access handler 160 may verify the user device 130 based on the credentials in the access request 305. If the verification is successful, the access handler 160 may determine to grant the user device 130 access to the selected portion of the datasets 180" for the permitted types of operations. Otherwise, if the verification is a failure, the access handler 160 may determine to restrict or deny the user device 130 access to the selected portion of the datasets 180" for the unpermitted types of operations.

With the selection, the access handler 160 may provide the user device 130 access to the portion of the datasets 180". In some embodiments, the provision of the access may be in response to determining to grant based on access privileges or in response to successful verifications of the authentication credentials. The access handler 160 may interface with the interface application 140 for the access. In some embodiments, the access handler 160 may transmit, provide, or otherwise send at least one response 310 to the user device 130. The response 310 may identify or include the portion of the datasets 180" to provide to the interface application 140 on the user device 130. In some embodiments, the access handler 160 may generate a new dataset 180 to include onto the data storage 175 when the access request 305 is to store new data. For instance, the new dataset 180 may include list of questionnaires to measure the safety, efficacy, or performance of the digital therapeutics application 120 to be provided to the participants of a given trial, as defined in the access request 305. The new dataset 180 may be included or identified in the response 310.

With the access, the interface application 140 on the user device 130 may generate an output for presentation using the datasets 180" identified in the response 310. The user device 130 may include a display to present, display, list, or otherwise show at least a portion of the datasets 180" on the display. The interface application 140 can control or manage displaying at least a portion of the datasets 180" A-N upon receipt of the same. In some embodiments, the interface application 140 may generate information based on the datasets 180". For example, the interface application 140 may present information identifying a plurality of measurements for the efficacy of the digital therapeutics application across a plurality of phases. The information may indicate whether a percentage of participants 210 reaching endpoints (e.g., behavioral, psychological, or mental) in relation to the condition to be addressed by the digital therapeutics application 140. In some embodiments, the interface application 140 may receive real-time data from the participant device 110.

In this manner, the data management service 105 together with the interface application 140 on the user device 130 may allow the user to participate in more than one digital therapeutics trial within the same infrastructure on their user device 130. This may offer the advantage of providing the user with a single and consistent user interface for multiple trials. The user may have local data that is shared among the various trials because they are integrated into a single data storage 175. For instance, the user may not need to re-enter personally identifiable information or personal health information multiple times for each phase 230 because the information is saved locally only once. Relative to approaches entailing the use of multiple, disparate databases to store data acquired from different phases and trials, the data management service 105 may reduce consumption of processing resources as well as space for data storage. The ability to access the datasets 180 on data storages 175 from one or more trials via the interface application 140 may also provide for improved quality of human-computer interaction (HCI) between the user and the other components of the system 100.

Figure 4:
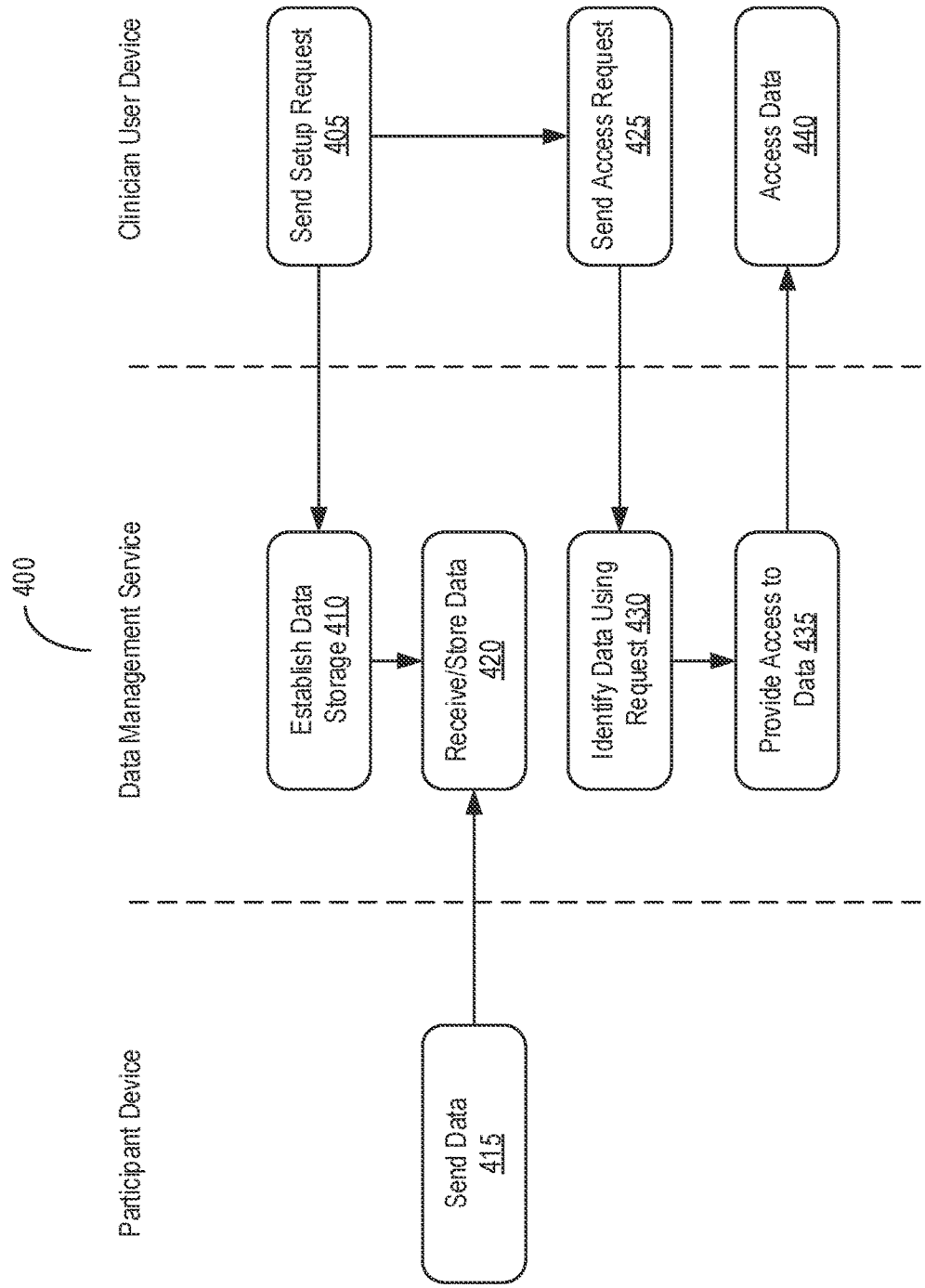
FIG. 4 depicts a block diagram for a process to communicate data and control access in the system for managing and coordinating data in accordance with an illustrative embodiment.

Referring now to FIG. 4, depicted is a flow diagram for a method 400 of managing and coordinating data. The method 400 may be performed by, but not limited to, any systems, devices, or components thereof described above with respect to FIGS. 1-3 or FIG. 7 below. At step 405, a clinician user device (e.g., the user device 130) sends a setup request (e.g., a trial setup request 205) to a data management service (e.g., a data management service 105). At step 410, the data management service establishes, creates, configures, or generates a data storage or dataset responsive to the setup request, or setup the data storage or dataset for trials of digital therapeutic applications. At step 415, a participant device (e.g., a participant device 110) can send data (e.g., application data 220, participant data 225) to the data management service. A step 420, the data management service can receive the data from the participant or the participant device. In response to receipt of the data, the data management service can store the data in the data storage. At step 425, the user device can send a request for access (e.g., access request 305) to the data to the data management service. At step 430, the data management service can identify the user device based at least in part on the request for access. At step 435, the data management service can provide the user device with access to the data (e.g., a response 310). At step 440, the user device may access the data to read, write, or edit.

Figure 5:
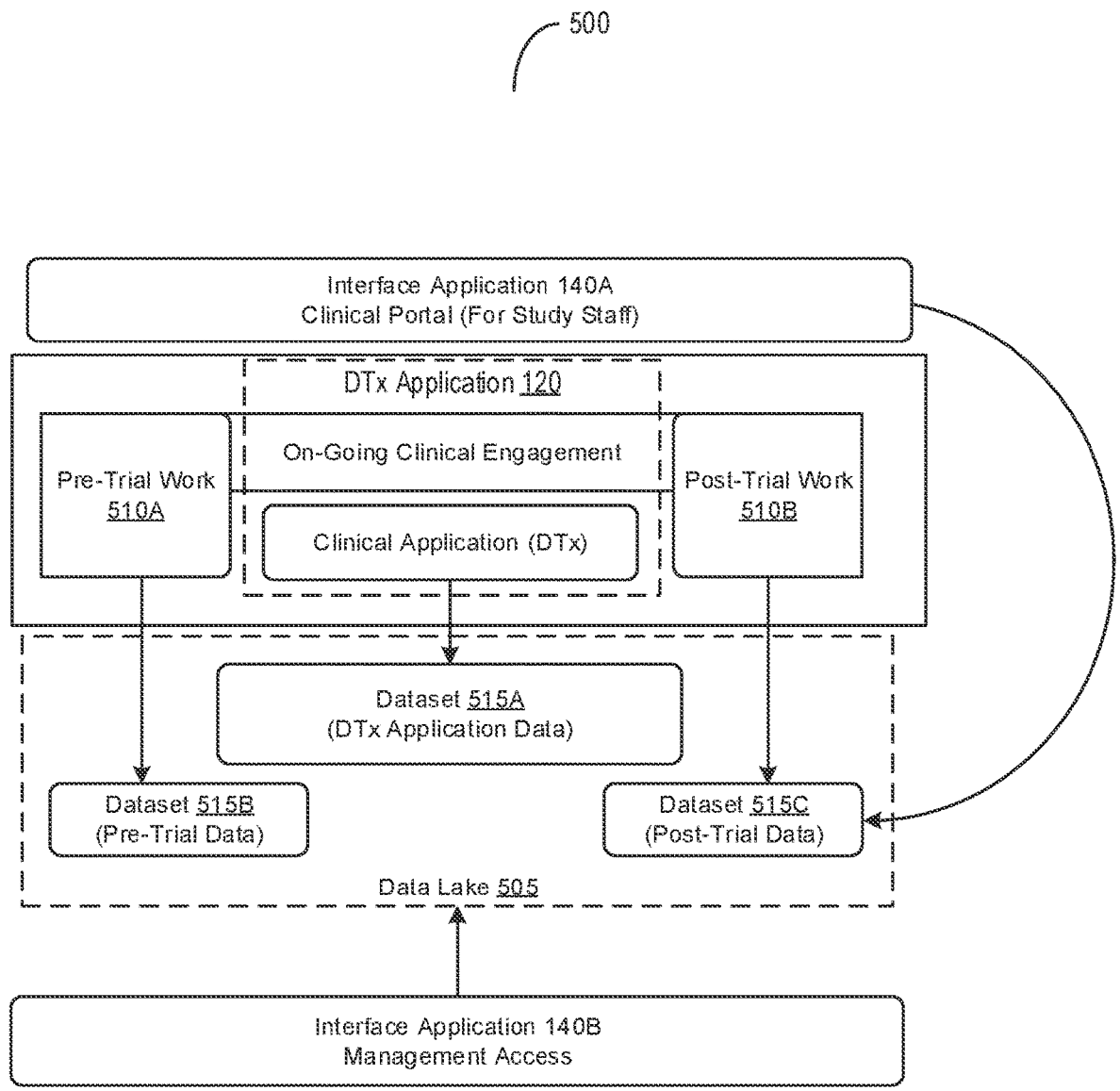
FIG. 5 each depict a block diagram showing example embodiments of a system for managing and coordinating data in accordance with an illustrative embodiment.

Referring now to FIG. 5, depicted is a block diagram of a system 500B for managing and coordinating data. The data storage may form a data lake 505. The data lake 505 may store a plurality of types of data, thereby integrating data for one or more trials of digital therapeutic applications. A first application 140A may be used by study staff to access at least a portion (e.g., dataset 515A for digital therapeutics application data, dataset 515B for pre-trial data, or dataset 515C for post-trial data) of the data lake 505 via a clinical portal. A second application 140B may be used by a clinician manager to access at least a portion (e.g., the datasets 515A-C) of the data lake 505 via, for example, a third party application (e.g., Snowflake). In some embodiments, the access of the first application 140A and the second application 140B may be determined based on, for example, privilege information identified in the access request 305.

Figure 6A:
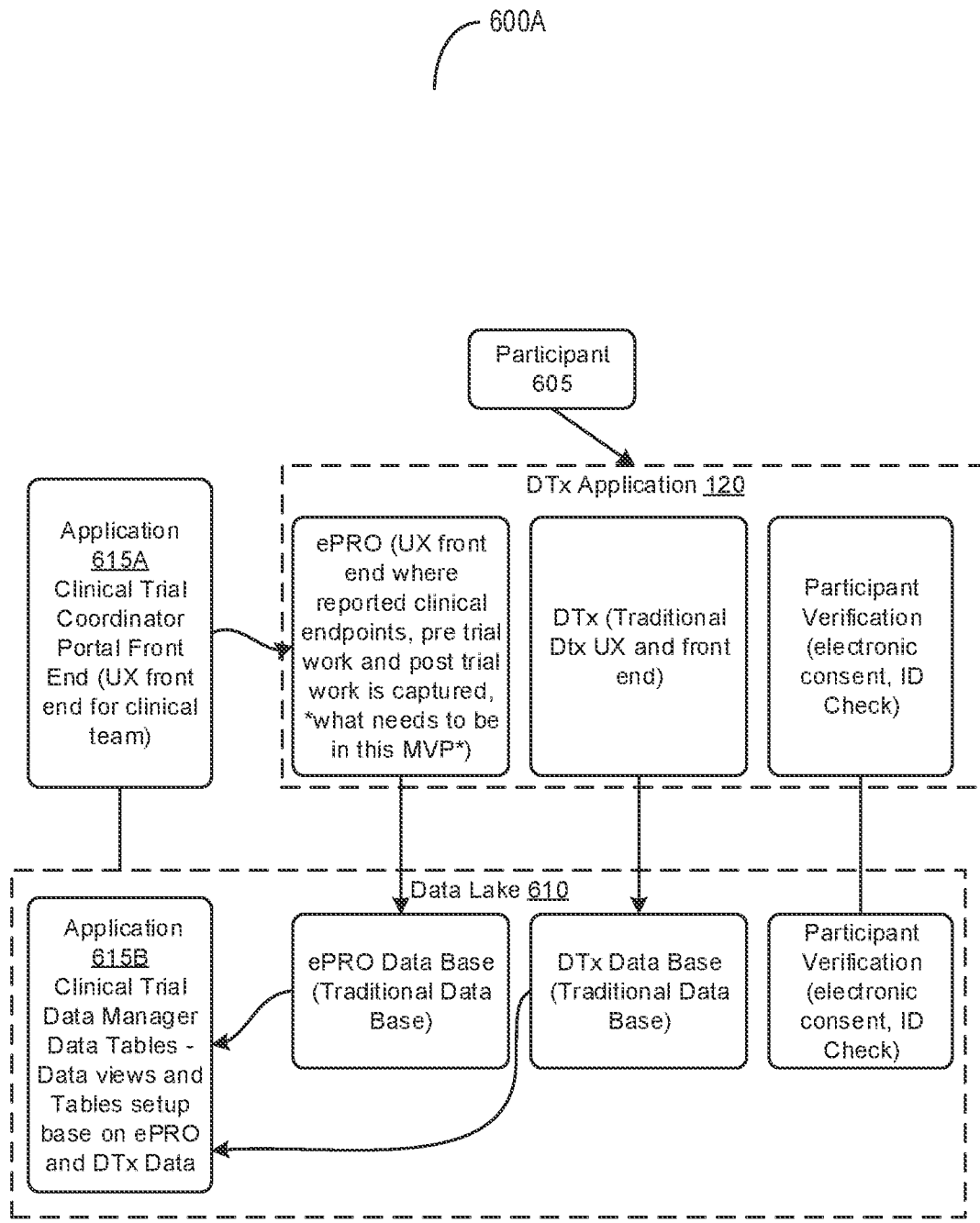
FIGS. 6A-B each depict a block diagram showing example embodiments of a system for managing and coordinating data in accordance with an illustrative embodiment.

Referring now to FIG. 6A, depicted is a block diagram 600A showing example embodiments of a system for managing and coordinating data. In some embodiments, the digital therapeutics application 120 and the data lake 610 may include ePRO, which can communicate data between the digital therapeutics application 120 and a data lake 610. The ePRO can capture or report clinical endpoints, pre-trial work, post-trial work, etc., from the digital therapeutics application 120, and can send to the data lake 610. In some embodiments, the digital therapeutics application 120 may include participant verification data (e.g., electronic consent, ID check, etc.) and can send to the data lake 610. The data lake 610 can receive, identify, store, or control the data received from the digital therapeutics application 120. For example, the data lake 610 may store an ePRO dataset, and participant verification dataset, as well as send at least portion of the same to applications 615. The applications 615 may include a first application 615A, and a second application 615B. Each of the first application 615A and the second application 615B may play a different role. For example, the first application 615A may be a front-end portal for the clinical team and may be used by a clinical trial coordinator.

Figure 6B:
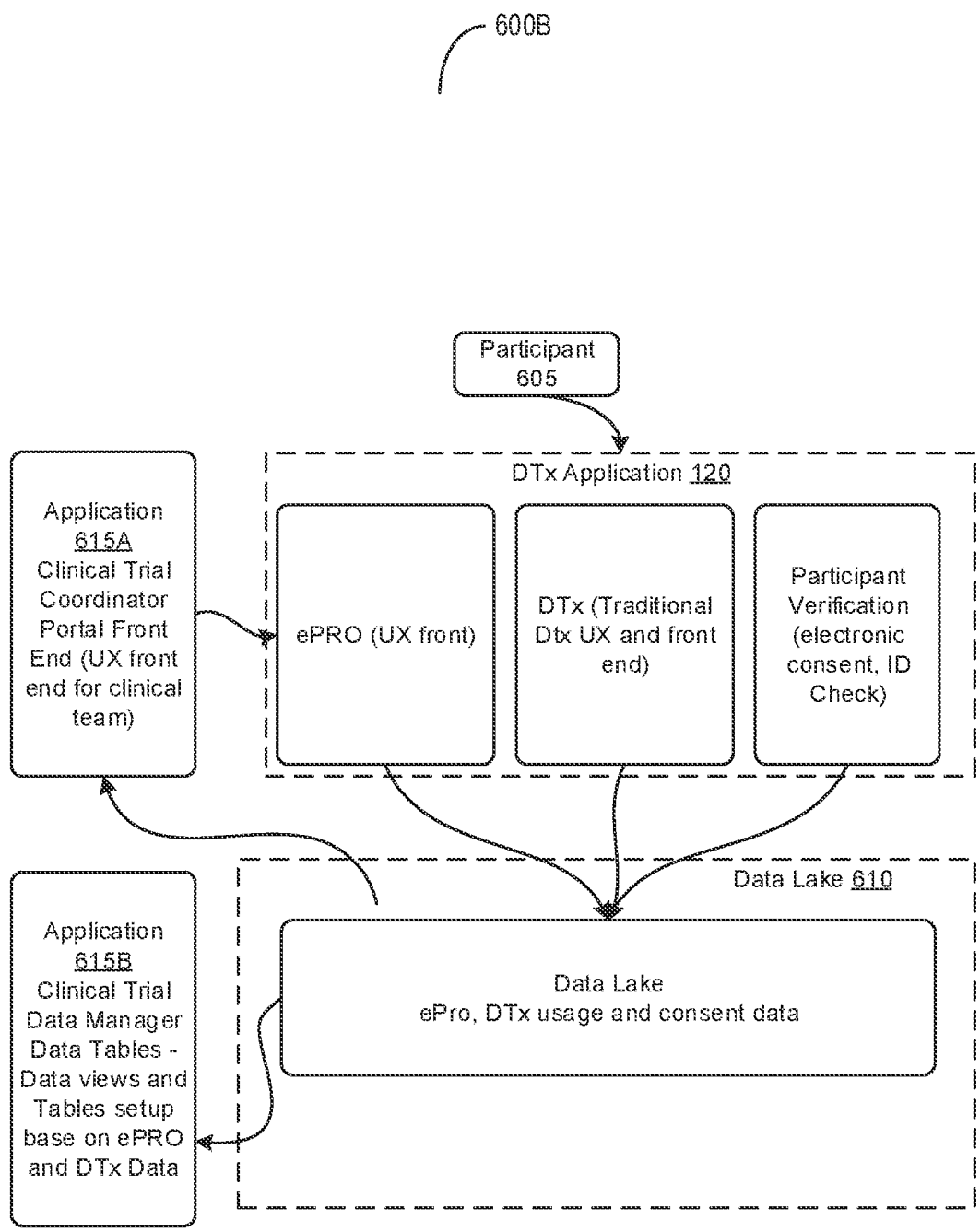

The first application 615A may have access to or manage the ePRO in the digital therapeutics application 120, while communicating data with the data lake 610. The second application 615B may be a part of the data lake 610, including data tables for digital therapeutics data, and may be used by a clinical trial data manager or a clinician. For example, the second application 615B may be connected to at least a portion of the data lake 610 (e.g., the ePRO, DTx dataset, etc.). In some embodiments, the second application 615B may provide the first application 615A with data for setting up, configuring, or establishing one or more datasets based at least in part on the ePRO dataset. In some embodiments, as shown in FIG. 6B, the application 615B may be excluded from the data lake 610. The data lake 610 may include the ePRO, DTx dataset, and participant dataset, and can provide the applications 615.

B. Network and Computing Environment

Figure 7:
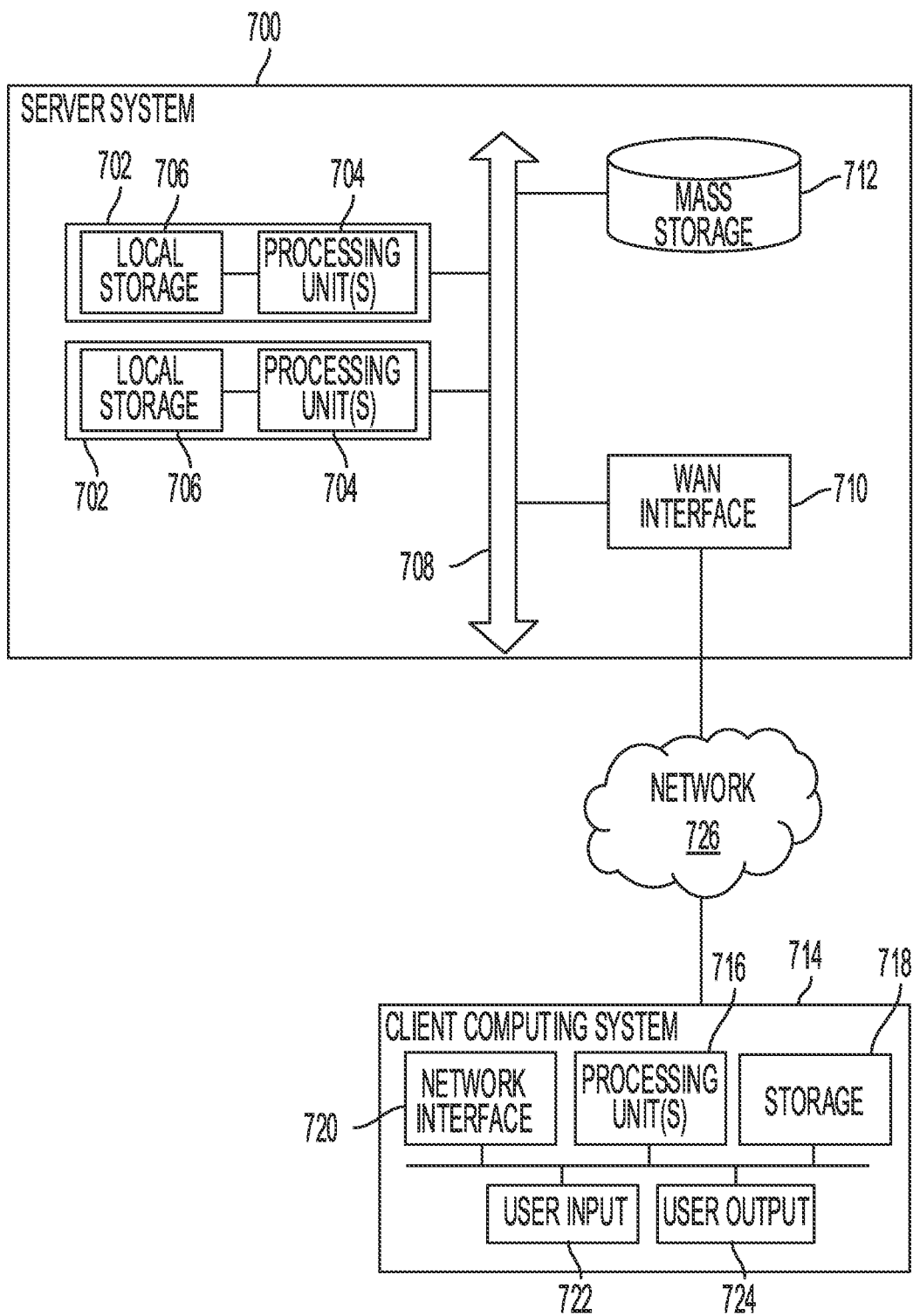
FIG. 7 is a block diagram of a server system and a client computer system in accordance with an illustrative embodiment.

Various operations described herein can be implemented on computer systems. FIG. 7 shows a simplified block diagram of a representative server system 700, client computer system 714, and network 726 usable to implement certain embodiments of the present disclosure. In various embodiments, server system 700 or similar systems can implement services or servers, described herein, or portions thereof. Client computer system 714 or similar systems can implement clients described herein. The system 100 described herein can be similar to the server system 700. Server system 700 can have a modular design that incorporates a number of modules 702 (e.g., blades in a blade server embodiment); while two modules 702 are shown, any number can be provided. Each module 702 can include processing unit(s) 704 and local storage 706.

Processing unit(s) 704 can include a single processor, which can have one or more cores, or multiple processors. In some embodiments, processing unit(s) 704 can include a general-purpose primary processor as well as one or more special-purpose co-processors such as graphics processors, digital signal processors, or the like. In some embodiments, some or all processing units 704 can be implemented using customized circuits, such as application specific integrated circuits (ASICs) or field programmable gate arrays (FPGAs). In some embodiments, such integrated circuits execute instructions that are stored on the circuit itself. In other embodiments, processing unit(s) 704 can execute instructions stored in local storage 706. Any type of processors in any combination can be included in processing unit(s) 704.

Local storage 706 can include volatile storage media (e.g., DRAM, SRAM, SDRAM, or the like) and/or non-volatile storage media (e.g., magnetic or optical disk, flash memory, or the like). Storage media incorporated in local storage 706 can be fixed, removable, or upgradeable as desired. Local storage 706 can be physically or logically divided into various subunits such as a system memory, a read-only memory (ROM), and a permanent storage device. The system memory can be a read-and-write memory device or a volatile read-and-write memory, such as dynamic random-access memory. The system memory can store some or all of the instructions and data that processing unit(s) 704 need at runtime. The ROM can store static data and instructions that are needed by processing unit(s) 704. The permanent storage device can be a non-volatile read-and-write memory device that can store instructions and data even when module 702 is powered down. The term "storage medium" as used herein includes any medium in which data can be stored indefinitely (subject to overwriting, electrical disturbance, power loss, or the like) and does not include carrier waves and transitory electronic signals propagating wirelessly or over wired connections.

In some embodiments, local storage 706 can store one or more software programs to be executed by processing unit(s) 704, such as an operating system and/or programs implementing various server functions such as functions of the system 100 or any other system described herein, or any other server(s) associated with system 100 or any other system described herein.

"Software" refers generally to sequences of instructions that, when executed by processing unit(s) 704, cause server system 700 (or portions thereof) to perform various operations, thus defining one or more specific machine embodiments that execute and perform the operations of the software programs. The instructions can be stored as firmware residing in read-only memory and/or program code stored in non-volatile storage media that can be read into volatile working memory for execution by processing unit(s) 704. Software can be implemented as a single program or a collection of separate programs or program modules that interact as desired. From local storage 706 (or non-local storage described below), processing unit(s) 704 can retrieve program instructions to execute and data to process in order to execute various operations described above.

In some server systems 700, multiple modules 702 can be interconnected via a bus or other interconnect 708, forming a local area network that supports communication between modules 702 and other components of server system 700. Interconnect 708 can be implemented using various technologies, including server racks, hubs, routers, etc.

A wide area network (WAN) interface 710 can provide data communication capability between the local area network (e.g., through the interconnect 708) and the network 726, such as the Internet. Other technologies can be used to communicatively couple the server system with the network 726, including wired (e.g., Ethernet, IEEE 802.3 standards) and/or wireless technologies (e.g., Wi-Fi, IEEE 802.11 standards).

In some embodiments, local storage 706 is intended to provide working memory for processing unit(s) 704, providing fast access to programs and/or data to be processed while reducing traffic on an interconnect 708. Storage for larger quantities of data can be provided on the local area network by one or more mass storage subsystems 712 that can be connected to an interconnect 708. Mass storage subsystem 712 can be based on magnetic, optical, semiconductor, or other data storage media. Direct attached storage, storage area networks, network-attached storage, and the like can be used. Any data stores or other collections of data described herein as being produced, consumed, or maintained by a service or server can be stored in a mass storage subsystem 712. In some embodiments, additional data storage resources may be accessible via a WAN interface 710 (potentially with increased latency).

Server system 700 can operate in response to requests received via a WAN interface 710. For example, one of modules 702 can implement a supervisory function and assign discrete tasks to other modules 702 in response to received requests. Work allocation techniques can be used. As requests are processed, results can be returned to the requester via a WAN interface 710. Such operation can generally be automated. Further, in some embodiments, a WAN interface 710 can connect multiple server systems 700 to each other, providing scalable systems capable of managing high volumes of activity. Other techniques for managing server systems and server farms (collections of server systems that cooperate) can be used, including dynamic resource allocation and reallocation.

The server system 700 can interact with various user-owned or user-operated devices via a wide-area network such as the Internet. An example of a user-operated device is shown in FIG. 7 as client computing system 714. The client computing system 714 can be implemented, for example, as a consumer device such as a smartphone, other mobile phone, tablet computer, wearable computing device (e.g., smart watch, eyeglasses), desktop computer, laptop computer, and so on.

For example, the client computing system 714 can communicate via a WAN interface 710. The client computing system 714 can include computer components such as the processing unit(s) 716, storage device 718, network interface 720, user input device 722, and user output device 724. The client computing system 714 can be a computing device implemented in a variety of form factors, such as a desktop computer, laptop computer, tablet computer, smartphone, other mobile computing device, wearable computing device, or the like.

The processing unit 716 and storage device 718 can be similar to processing unit(s) 704 and local storage 706 described above. Suitable devices can be selected based on the demands to be placed on client computing system 714; for example, the client computing system 714 can be implemented as a "thin" client with limited processing capability or as a high-powered computing device. The client computing system 714 can be provisioned with program code executable by processing unit(s) 716 to enable various interactions with the server system 700.

Network interface 720 can provide a connection to the network 726, such as a wide area network (e.g., the Internet) to which WAN interface 710 of server system 700 is also connected. In various embodiments, network interface 720 can include a wired interface (e.g., Ethernet) and/or a wireless interface implementing various RF data communication standards such as Wi-Fi, Bluetooth, or cellular data network standards (e.g., 3G, 4G, LTE, etc.).

User input device 722 can include any device (or devices) via which a user can provide signals to client computing system 714; client computing system 714 can interpret the signals as indicative of particular user requests or information. In various embodiments, user input device 722 can include any or all of a keyboard, touch pad, touch screen, mouse or other pointing device, scroll wheel, click wheel, dial, button, switch, keypad, microphone, and so on.

User output device 724 can include any device via which client computing system 714 can provide information to a user. For example, user output device 724 can include display-to-display images generated by or delivered to client computing system 714. The display can incorporate various image generation technologies, e.g., a liquid crystal display (LCD), light-emitting diode (LED) display including organic light-emitting diodes (OLED), projection system, cathode ray tube (CRT), or the like, together with supporting electronics (e.g., digital-to-analog or analog-to-digital converters, signal processors, or the like). Some embodiments can include a device such as a touchscreen that function as both input and output device. In some embodiments, other user output devices 724 can be provided in addition to or instead of a display. Examples include indicator lights, speakers, tactile "display" devices, printers, and so on.

Some embodiments include electronic components, such as microprocessors, storage, and memory that store computer program instructions in a computer readable storage medium. Many of the features described in this specification can be implemented as processes that are specified as a set of program instructions encoded on a computer readable storage medium. When these program instructions are executed by one or more processing units, they cause the processing unit(s) to perform various operations indicated in the program instructions. Examples of program instructions or computer code include machine code, such as is produced by a compiler, and files including higher-level code that are executed by a computer, an electronic component, or a microprocessor using an interpreter. Through suitable programming, processing unit(s) 704 and 716 can provide various functionality for server system 700 and client computing system 714, including any of the functionality described herein as being performed by a server or client, or other functionality.

It will be appreciated that server system 700 and client computing system 714 are illustrative and that variations and modifications are possible. Computer systems used in connection with embodiments of the present disclosure can have other capabilities not specifically described here. Further, while server system 700 and client computing system 714 are described with reference to particular blocks, it is to be understood that these blocks are defined for convenience of description and are not intended to imply a particular physical arrangement of component parts. For instance, different blocks can be but need not be located in the same facility, in the same server rack, or on the same motherboard. Further, the blocks need not correspond to physically distinct components. Blocks can be configured to perform various operations, e.g., by programming a processor or providing appropriate control circuitry, and various blocks might or might not be reconfigurable depending on how the initial configuration is obtained. Embodiments of the present disclosure can be realized in a variety of apparatus including electronic devices implemented using any combination of circuitry and software.

While the disclosure has been described with respect to specific embodiments, one skilled in the art will recognize that numerous modifications are possible. Embodiments of the disclosure can be realized using a variety of computer systems and communication technologies, including but not limited to specific examples described herein. Embodiments of the present disclosure can be realized using any combination of dedicated components and/or programmable processors and/or other programmable devices. The various processes described herein can be implemented on the same processor or different processors in any combination. Where components are described as being configured to perform certain operations, such configuration can be accomplished, e.g., by designing electronic circuits to perform the operation, by programming programmable electronic circuits (such as microprocessors) to perform the operation, or any combination thereof. Further, while the embodiments described above may make reference to specific hardware and software components, those skilled in the art will appreciate that different combinations of hardware and/or software components may also be used and that particular operations described as being implemented in hardware might also be implemented in software or vice versa.

Computer programs incorporating various features of the present disclosure may be encoded and stored on various computer readable storage media; suitable media include magnetic disk or tape, optical storage media such as compact disk (CD) or digital versatile disk (DVD), flash memory, and other non-transitory media. Computer readable media encoded with the program code may be packaged with a compatible electronic device, or the program code may be provided separately from electronic devices (e.g., via Internet download or as a separately packaged computer-readable storage medium).

Thus, although the disclosure has been described with respect to specific embodiments, it will be appreciated that the disclosure is intended to cover all modifications and equivalents within the scope of the following claims.

What is claimed is:

1. A method of managing access to data associated with trials for digital therapeutics on participants, comprising:
receiving, by a server, from a user device, a request to define a plurality of parameters for at least one trial, the plurality of parameters identifying at least one of a digital therapeutic, a plurality of phases, or a respective endpoint for each of the plurality of phases;
establishing, by the server, a data lake comprising a data storage to store a plurality of datasets in at least one of a structured format or an unstructured format for the at least one trial in accordance with the plurality of parameters;
maintaining, by the server, for multiple digital therapeutics, the data lake for a plurality of phases associated with a trial for a digital therapeutic provided by a digital therapeutic application to a plurality of participants, the plurality of phases including (a) a pre-trial phase prior to commencing the trial for the digital therapeutic, (b) a trial phase during the trial, and (c) a post-trial phase subsequent to completion of the trial for the digital therapeutic, wherein the data lake maintains the data of the plurality of phases in a centralized manner, the data lake comprising:
(i) a plurality of datasets from the pre-trial phase,
(ii) a plurality of datasets from the trial phase, and
(iii) a plurality of datasets from the post-trial phase;
receiving, by the server, from the user device, an additional request associated with a participant or group of participants, an endpoint, and a phase of the plurality of phases for which the plurality of datasets is to be accessed;
selecting, by the server, a corresponding portion of the plurality of datasets based on the additional request, wherein the corresponding portion is selected by identifying linked data linked by an association between a plurality of trials; and
providing, by the server, to the user device, the corresponding portion of the plurality of datasets in the data lake.

2. The method of claim 1, further comprising:
identifying, by the server, a plurality of trials associated with a corresponding plurality of conditions of the plurality of participants provided with the digital therapeutic; and
establishing, by the server, a plurality of data storages for the corresponding plurality of trials.

3. The method of claim 1, further comprising:
receiving, by the server, from the user device, a second request to associate the data storage with a second data storage, the second data storage comprising a second plurality of datasets from a second trial separate from the trial associated with the data storage; and
linking, by the server, responsive to the second request, the second data storage with the data storage to provide the user device access to the data storage and the second data storage.

4. The method of claim 1, further comprising identifying, by the server, from a plurality of access privileges, an access privilege for a user associated with the user device, and wherein providing the corresponding portion further comprises providing the user device access to the portion of the plurality of datasets, responsive to the access privilege defining that the user is permitted to access the portion.

5. The method of claim 1, wherein receiving the request further comprises:
receiving the request identifying a questionnaire to add to the phase of the plurality of phases; and
generating, by the server, at least one dataset identifying the questionnaire to add to at least one corresponding portion of the plurality of datasets.

6. The method of claim 1, wherein maintaining the data storage further comprises removing, from the data storage, a first dataset in one portion of the plurality of datasets corresponding to a second dataset in another portion of the plurality of datasets.

7. The method of claim 1, wherein receiving the request further comprises receiving the request identifying a participant of the plurality of participants for which the plurality of datasets is to be accessed;
wherein providing the access further comprises correlating, within the plurality of datasets on the data storage, one or more datasets associated with the participant identified in the request.

8. The method of claim 1, wherein at least one of the plurality of datasets are generated using at least one of electronic data capture (EDC), identity verification, and informed consent.

9. The method of claim 1, wherein at least one of the plurality of participants is administered with a pharmaceutical to address a condition, at least partially concurrently with use of the digital therapeutic.

10. A system for managing access to data associated with trials for digital therapeutics on participants, comprising:
at least one server having one or more processors coupled with memory, configured to:
receive, from a user device, a request to define a plurality of parameters for at least one trial, the plurality of parameters identifying at least one of a digital therapeutic, a plurality of phases, or a respective endpoint for each of the plurality of phases;
establish a data lake comprising a data storage to store a plurality of datasets in at least one of a structured format or an unstructured format for the at least one trial in accordance with the plurality of parameters;
maintain, for multiple digital therapeutics, the data lake for a plurality of phases associated with a trial for a digital therapeutic provided by a digital therapeutic application to a plurality of participants, the plurality of phases including (a) a pre-trial phase prior to commencing the trial for the digital therapeutic, (b) a trial phase during the trial, and (c) a post-trial phase subsequent to completion of the trial for the digital therapeutic, wherein the data lake maintains the data of the plurality of phases in a centralized manner, the data lake comprising:
(i) a plurality of datasets from the pre-trial phase,
(ii) a plurality of datasets from the trial phase, and
(iii) a plurality of datasets from the post-trial phase;
receive, from the user device, an additional request associated with a participant or group of participants, an endpoint, and a phase of the plurality of phases for which the plurality of datasets is to be accessed;
select a corresponding portion of the plurality of datasets based on the additional request, wherein the corresponding portion is selected by identifying linked data linked by an association between a plurality of trials; and provide, to the user device, the corresponding portion of the plurality of datasets in the data lake.

11. The system of claim 10, wherein the at least one server is further configured to:
identify a plurality of trials associated with a corresponding plurality of conditions of the plurality of participants provided with the digital therapeutic; and
establish a plurality of data storages for the corresponding plurality of trials.

12. The system of claim 10, wherein the at least one server is further configured to:
receive, from the user device, a second request to associate the data storage with a second data storage, the second data storage comprising a second plurality of datasets from a second trial separate from the trial associated with the data storage; and
link, responsive to the second request, the second data storage with the data storage to provide the user device access to the data storage and the second data storage.

13. The system of claim 10, wherein the at least one server is further configured to:
identify, from a plurality of access privileges, an access privilege for a user associated with the user device; and
wherein to provide the corresponding portion, the at least one server is configured to provide, to the user device associated with the user, access to the portion of the plurality of datasets, responsive to the access privilege defining that the user is permitted to access the portion.

14. The system of claim 10, wherein the at least one server is further configured to:
receive the request identifying a questionnaire to add to the phase of the plurality of phases; and
generate at least one dataset identifying the questionnaire to add to at least one corresponding portion of the plurality of datasets.

15. The system of claim 10, wherein the at least one server is further configured to remove, from the data storage, a first datasets in one portion of the plurality of datasets corresponding to a second dataset in another portion of the plurality of datasets.

16. The system of claim 10, wherein the at least one server is further configured to:
receive the request identifying a participant of the plurality of participants for which the plurality of datasets is to be accessed;
correlate, within the plurality of datasets on the data storage, one or more datasets associated with the participant identified in the request.

17. The system of claim 10, wherein at least one of the plurality of datasets are generated using at least one of electronic data capture (EDC), identity verification, and informed consent.

18. The system of claim 10, wherein at least one of the plurality of participants is administered with a pharmaceutical to address a condition, at least partially concurrently with use of the digital therapeutic.

* * * * *